US00PP32466P2

(12) United States Plant Patent
Geoghegan

(10) Patent No.: US PP32,466 P2
(45) Date of Patent: Nov. 17, 2020

(54) STRAWBERRY PLANT NAMED 'LADY EMMA'

(50) Latin Name: ***Fragaria* x *ananassa* (Duch.)**
Varietal Denomination: Lady Emma

(71) Applicant: S&A Soft Fruits Ltd., Marden, Herefordshire (GB)

(72) Inventor: Irene Geoghegan, Dundee (GB)

(73) Assignee: S&A Soft Fruits Ltd., Marden (GB)

( * ) Notice: Subject to any disclaimer, the term of this patent is extended or adjusted under 35 U.S.C. 154(b) by 0 days.

(21) Appl. No.: 16/501,678

(22) Filed: May 21, 2019

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./209, 208
CPC ..... A01H 5/08; A01H 5/0893; A01H 6/74; A01H 6/7409
See application file for complete search history.

(56) References Cited

PUBLICATIONS

Upov Pluto Plant Variety Database Apr. 8, 2020, retrieved on Apr. 13, 2020, retrieved from the Internet at https://www.upov.int/pluto/en/index.jsp, one page. (Year: 2020).*

* cited by examiner

*Primary Examiner* — June Hwu
(74) *Attorney, Agent, or Firm* — The Webb Law Firm

(57) ABSTRACT

A new and distinct strawberry plant is provided which exhibits a compact growth habit, large and glossy fruits with a consistent conic shape, and strong remontant behavior.

4 Drawing Sheets

Botanical classification: *Fragaria* x *ananassa* (Duch.).
Varietal denomination: 'Lady Emma'.

BACKGROUND OF THE INVENTION

The present invention comprises a new and distinct variety of strawberry plant botanically classified as *Fragaria* x *ananassa* (Duch.) and known by the varietal name 'Lady Emma'. The new variety was originally referred to as RD015-016-2012. The new variety is the result of a cross between strawberry seedling referred to as SA22 (female parent, unpatented) and strawberry seedling referred to as SA11 (male parent, unpatented). The resultant cross produced 'Lady Emma' in July of 2013 in Herefordshire, United Kingdom. The purpose of the breeding program was to develop novel everbearing and day neutral strawberry varieties. Subsequently, the new variety was asexually reproduced via stolons in Herefordshire, United Kingdom in August of 2013. The new variety has been trial and field tested and has been found to retain its distinctive characteristics and remain true to type through successive asexual propagations. The new variety has not been evaluated under all possible environmental conditions. The phenotype may vary with variations in environment without a change in the genotype of the plant.

The new variety is similar to its female parent in having a compact growth habit and providing a high yield of consistently conic-shaped fruit. However, 'Lady Emma' differs from its female parent in exhibiting larger flowers and fruit, occasional petal adhesion, stronger remontant behavior, and flowers displayed at the level of the leaf canopy. The new variety is similar to its male parent in having a consistent shape throughout harvest and providing attractive, glossy fruit. However, 'Lady Emma' differs from its male parent in providing higher fruit yields with a more conical shape, and exhibiting a more compact architecture with larger flowers.

When compared to strawberry variety named 'Elsanta' (unpatented), 'Elsanta' is non-remontant, with paler and more orange-colored fruit. Further, the fruit of 'Elsanta' varies dramatically in size between its primary and secondary positions. In comparison, 'Lady Emma' is remontant, with a more compact plant architecture, darker green leaves, and larger, more consistent berry size having a conical shape.

The following characteristics also distinguish the new variety from other strawberry varieties known to the breeder:

- Very compact plant architecture/growth habit;
- Consistently large, glossy fruit with occasional petal adhesion;
- Consistent conic-shaped fruit with a very low proportion of misshapes;
- Early fruit ripening;
- Strong remontant behavior—not very vegetative; and
- Broad shouldered fruit with a typically inverted calyx.

DESCRIPTION OF THE DRAWINGS

The accompanying photographic drawings illustrate the new variety at approximately 9 months of age, with the color being as nearly true as is possible with color illustrations of this type. "015-016" shown in FIGS. 1 and 2 is shorthand for the Applicant's internal alphanumeric designation of "RD015-016-2012" for 'Lady Emma'. It should be noted that colors may vary with growing conditions and time of year.

DESCRIPTION OF THE PLANT

Figure 1:
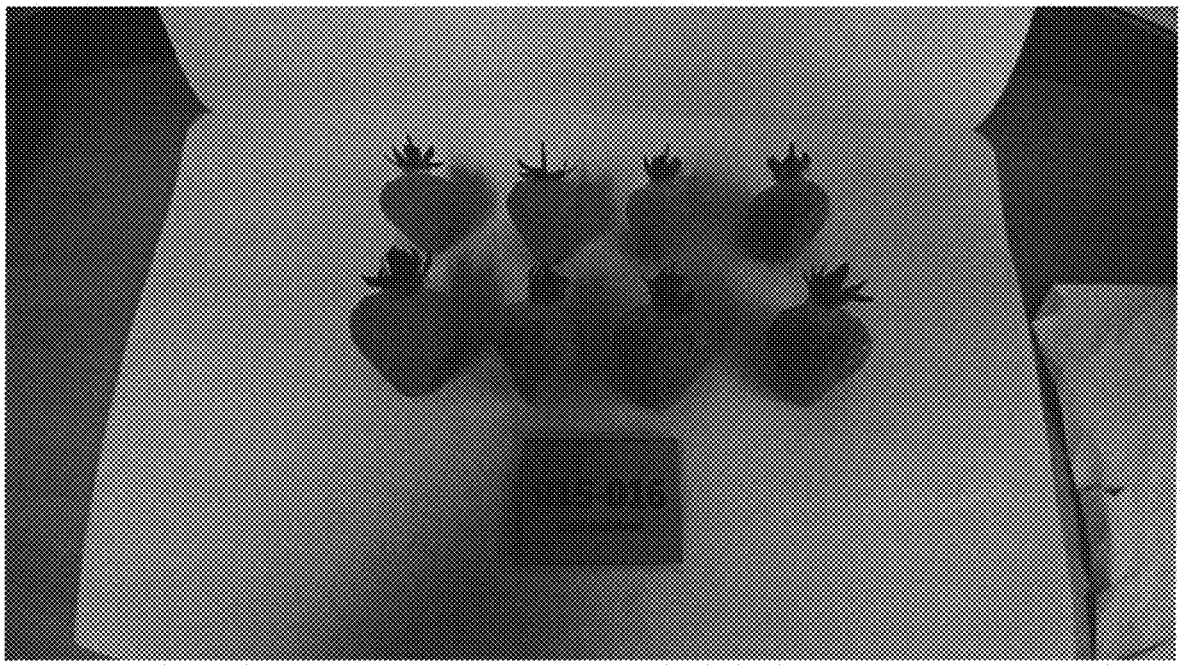
FIG. 1 is a photograph of multiple fruits of the new variety.
Figure 2:
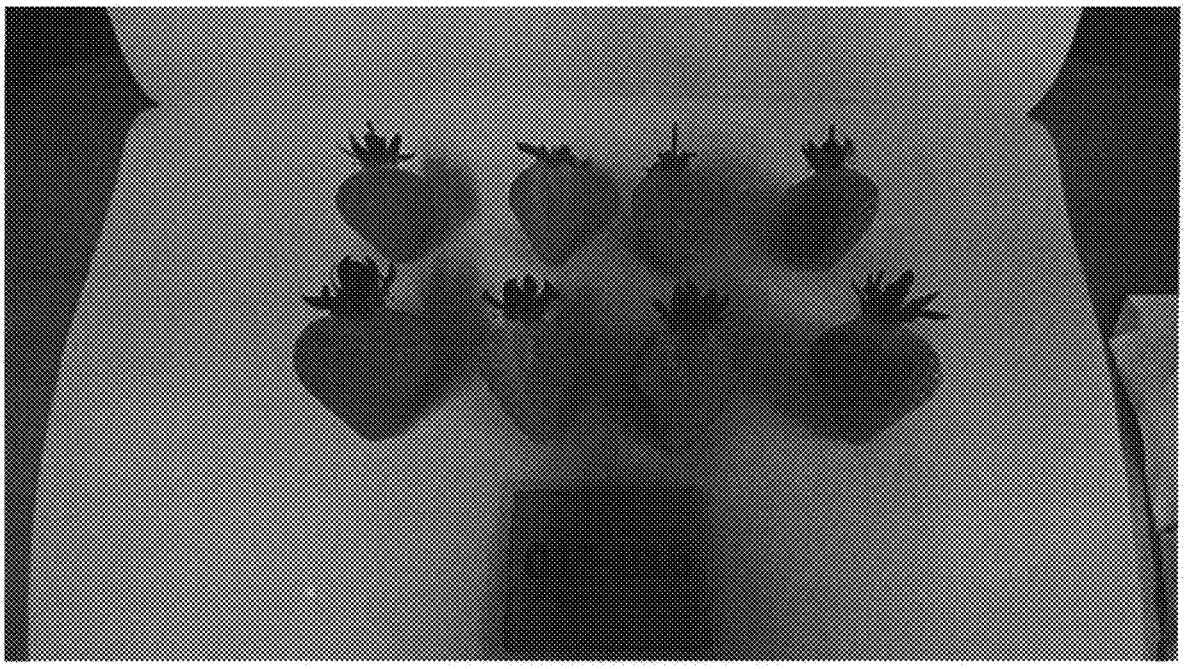
FIG. 2 is a photograph of whole and halved fruits of the new variety.
Figure 3:
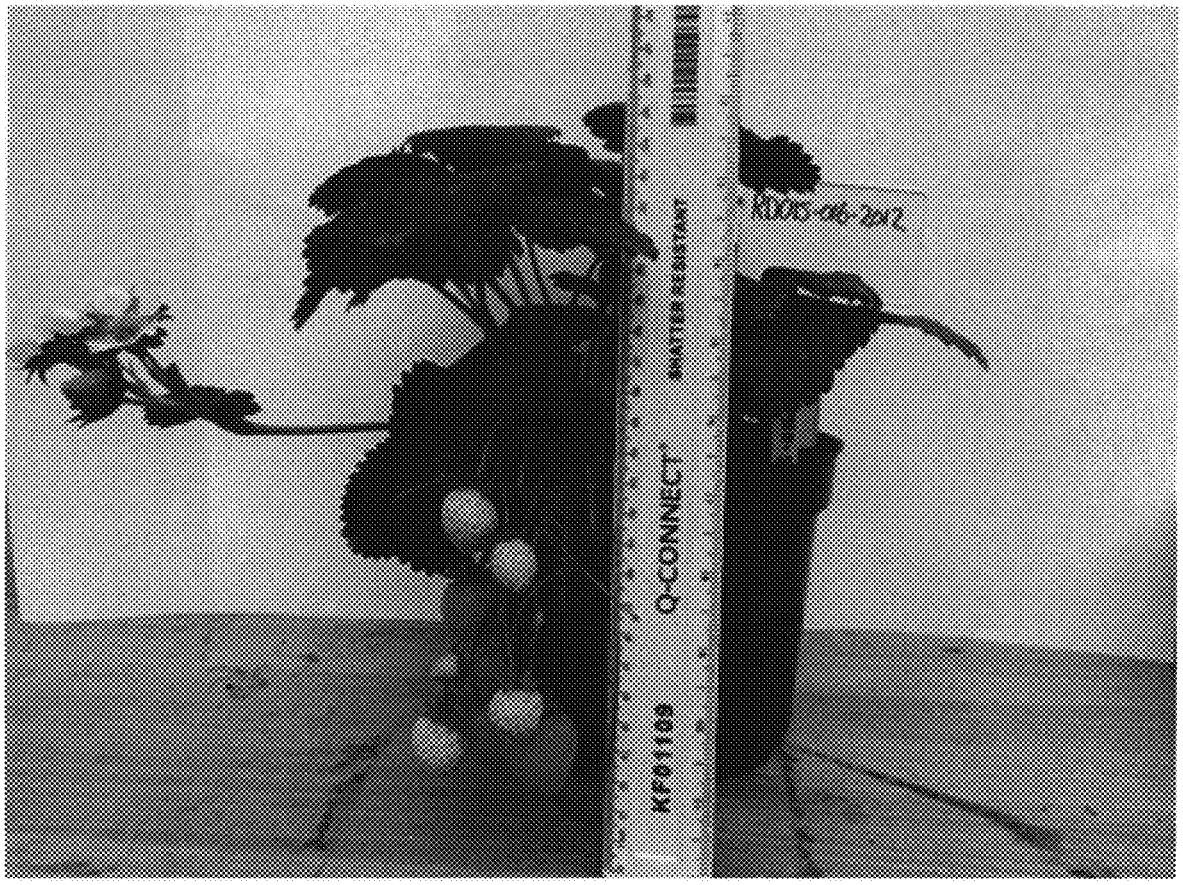
FIG. 3 is a photograph of an entire plant of the new variety.
Figure 4:
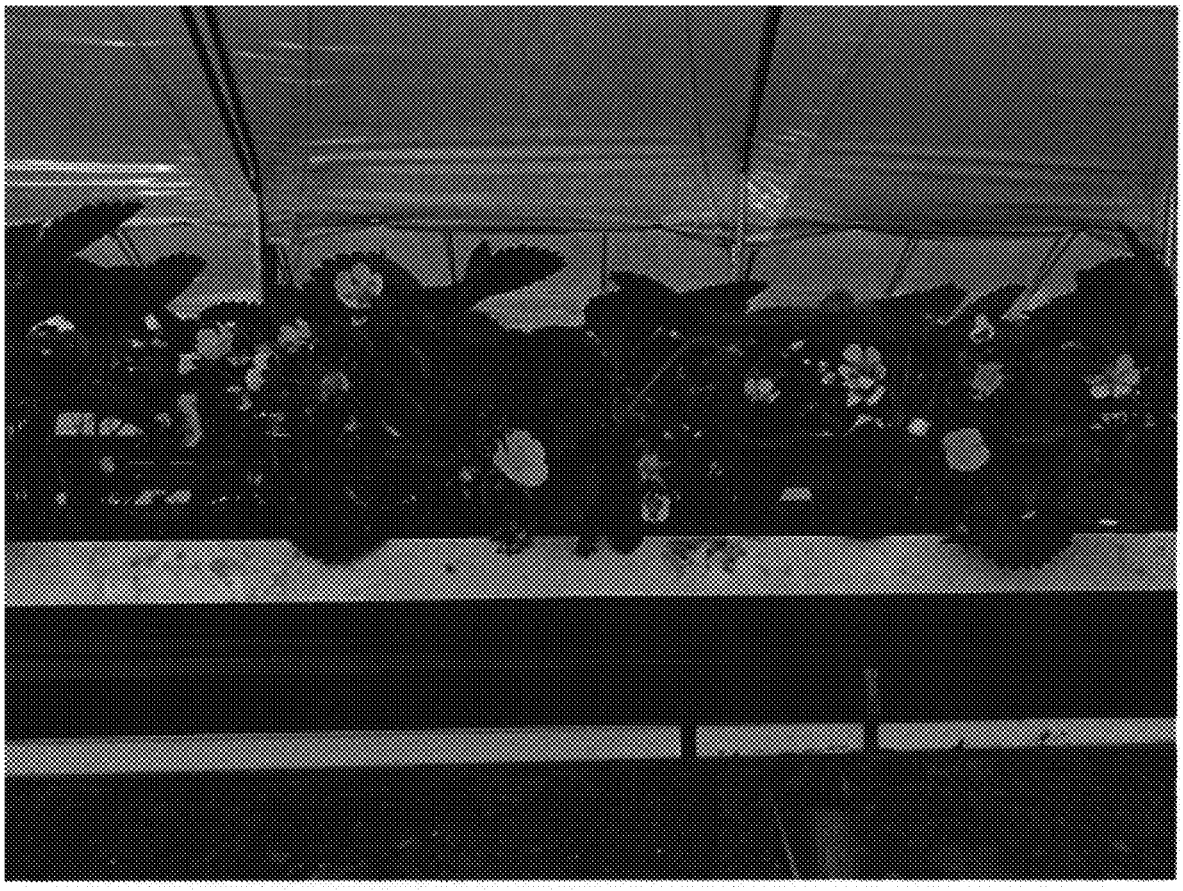
FIG. 4 is a photograph of multiple plants of the new variety.

The following detailed description sets forth the characteristics of the new cultivar. The new variety was grown under glasshouse protection in 2 liter containers in Llandow, the United Kingdom with an average day temperature of 18° C. and an average night temperature of 12° C. The new variety was approximately 9 months of age when described. Color references are primarily to The Sixth Edition (2015) of The R.H.S. Colour Chart of The Royal Horticultural Society of London and were identified under natural light.

PLANT

Time to initiate roots: 48 hours at an average temperature of 20° C.

Time to produce a rooted plant: 30 days at an average temperature of 20° C.

Rooting habit: Reasonably vigorous.

Stolons: Few present, with no anthocyanin coloration and moderate pubescence.

Plant form: Compact and partially mounded.

Height (from soil to top of plant): Typically from 20-25 cm.

Plant diameter: 35-45 cm.

Vigor: Moderate.

Disease/pest resistance: Resistant to powdery mildew and crown rot. Petioles are potentially susceptible to *Botrytis cinerea* (grey mold), depending on growing conditions.

Weather tolerance: Plants perform best in a protected environment, but do exhibit high temperature tolerance.

Foliage:

- *Arrangement.*—Basal rosette; upwardly facing.
- *Average number of leaves per plant.*—7-14.
- *Number of leaflets per leaf.*—Generally 3.
- *Whole leaf length.*—17-30 cm.
- *Whole leaf width.*—13-16 cm.
- *Leaf blistering.*—Weak.
- *Leaf glossiness.*—Moderate.
- *Inflorescence position.*—Same level as foliage.
- *Petiole.*—Length: 13-21 cm. Diameter: 2.3-3.1 mm. Color: RHS 145A. Texture: Pubescence outwardly/laterally facing.
- *Stipule.*—Average number per leaf: Usually 2-3. Length: 2-3 cm. Width: 7.2 mm. Color: Absent or very weak pigmentation that is close to RHS 145D.
- *Color.*—Young leaflets: Upper surface: Close to RHS 144A. Lower surface: Close to RHS 144B. Mature leaflets: Upper surface: RHS 137A. Lower surface: RHS 138B.
- *Lateral leaflets.*—Length: 6-8 cm. Width: 6-8 cm. Shape of leaf (generally): Typically orbicular, basally asymmetrical, cross-sectionally concave. Shape of apex: Obtuse. Shape of base: Between acute and obtuse. Texture (both surfaces): Light covering of pubescence present. Aspect: Upright. Margin type: Crenate.
- *Terminal leaflets.*—Length: 7-9 cm. Width: 6-8 cm. Shape of leaf (generally): Orbicular to rounded, cross-sectionally concave. Shape of apex: Rounded/obtuse. Shape of base: Acute. Texture (both surfaces): Light covering of pubescence present. Aspect: Upright. Margin type: Crenate.
- *Veins.*—Venation pattern: Pinnate. Color: Upper surface: RHS 144D. Lower surface: Between RHS 145C and 145D.

Fruit:

- *Harvest season.*—From May-December in Herefordshire, United Kingdom.
- *Plant temperature tolerance.*—From −3° C. to +38° C.
- *Shipping quality.*—Able to be shipped via refrigerated transport (+4° C.).
- *Fruit storage life.*—Up to 7 days post-harvest.
- *Use.*—Primarily fresh market.
- *Productivity* (*total fruit weight per plant*).—2.4 Kg per plant.
- *Number of fruit per fruiting lateral.*—4-8.
- *Surface color.*—Immature: RHS 150D. Maturing: RHS 32B. Fully mature: RHS 44B. Evenness of color: Typically ripens darker on side directly facing light source.
- *Taste.*—Good.
- *Aroma.*—Faintly fruity and sometimes absent.
- *Length.*—2.8-5.1 cm.
- *Width.*—2.6-3.9 cm.
- *Length/width ratio.*—Longer than wide.
- *Overall shape.*—Conic.
- *Glossiness.*—Strong.
- *Evenness of fruit surface.*—Even.
- *Weight.*—Average of 19 g.
- *Achene position.*—Beneath surface level.
- *Achene color.*—From RHS 11A to RHS 171B.
- *Average number of achenes per berry.*—340.
- *Width of band without achenes at the top of the fruit/just below the calyx.*—5.9-8.0 mm.
- *Attachment of calyx to the fruit.*—Slightly raised.
- *Sepal attitude.*—Upwards.
- *Flesh firmness.*—Medium to firm.
- *Flesh color* (*not including fruit core*).—Close to RHS 33A.
- *Fruit core color.*—Close to RHS 44A.
- *Cavity size.*—Small.
- *Fruiting truss length.*—18-28 cm.
- *Fruiting truss diameter.*—2-4 mm.
- *Fruiting truss color.*—RHS 145A.
- *Brix reading.*—Average of 9.4.
- *Acidity level.*—Average of 0.64.

Reproductive organs:

- *Stamens.*—Number per flower: 19-21. Length: 2.1-3.9 mm. Width: 1.0-1.4 mm.
- *Anthers.*—Apex shape: Rounded. Base Shape: Cordate. Length: 1.6-2.0 mm. Width: 1.2-1.4 mm. Color: Edge: Close to RHS 20A. Center: Close to RHS 7A.
- *Stigma.*—Texture: Lightly papillose. Shape: Rounded to ovate. Color: Close to RHS 152C.
- *Style.*—Length: About 1.8 mm. Color: RHS 4A.
- *Ovary.*—Texture: Pubescence present. Length: About 0.6 mm. Color: With seed: RHS 150C. Without seed: RHS 150B.
- *Stolon.*—Length: Mother plant to first stolon-plant: 33-38 cm. Mother plant to second stolon-plant:

67-85 cm. Diameter: 0.3-0.5 cm. Color: Between RHS 144D and RHS 145A.

Flowers:

*Natural flowering season.*—From April-November in Herefordshire, the United Kingdom.

*Number of flowers per plant.*—30-45.

*Fragrance.*—None present.

*Longevity.*—4-5 days.

*Flower description.*—Rotate flowers arranged singly at lateral apices that are cupped slightly upwards and with little to no overlap of petals.

*Flower height.*—7-10 mm.

*Flower diameter.*—1.8-2.4 mm.

*Petals.*—Number per flower: 5. Shape: Globose to obovate at base. Length: 9.0-10.5 mm. Width: 8-9 mm. Apex: Rounded. Base: Acute point. Margin: Entire. Texture (both surfaces): Smooth, with no pubescence present. Color: Mature petal: Upper surface: RHS NN155D. Lower surface: RHS NN155D (can accumulate anthocyanin close to RHS 67A on apex lower surface under certain growing conditions). Young petal: Upper surface: RHS 155C. Lower surface: RHS 155C.

*Sepals.*—Number per flower: 10. Length: 7-10 mm. Width: 3 mm. Shape: Lanceolate with typically a single point; can be multi-pointed on primary flowers. Number: 10. Apex: Acute. Margin: Typically entire; occasionally exhibits a serrated tip predominantly on primary flowers. Texture: Pubescence present on both upper and lower surfaces. Color: Mature sepal: Upper surface: Close to RHS 137A. Lower surface: Close to RHS 138B. Young sepal: Upper surface: Close to RHS 143A. Lower surface: Close to RHS 143C.

*Buds.*—Length: 9-10 mm. Diameter: 6-7 mm. Shape: Longer than broader. Color: RHS 145A.

I claim:

1. A new and distinct variety of strawberry plant, as is herein illustrated and described.

* * * * *